US007563265B1

(12) United States Patent
Murphy

(10) Patent No.: US 7,563,265 B1
(45) Date of Patent: Jul. 21, 2009

(54) APPARATUS FOR STRENGTHENING VERTEBRAL BODIES

(76) Inventor: Kieran P. J. Murphy, 119 Beechdale Rd., Baltimore, MD (US) 21210

( * ) Notice: Subject to any disclaimer, the term of this patent is extended or adjusted under 35 U.S.C. 154(b) by 1495 days.

(21) Appl. No.: 09/594,685

(22) Filed: Jun. 16, 2000

Related U.S. Application Data

(63) Continuation-in-part of application No. 09/425,480, filed on Oct. 22, 1999, now Pat. No. 6,273,916.

(30) Foreign Application Priority Data

Sep. 2, 1999 (CA) .................................... 2281335
Oct. 22, 1999 (CA) .................................... 2287112

(51) Int. Cl.
*A61B 17/58* (2006.01)
(52) U.S. Cl. ...................................................... 606/92
(58) Field of Classification Search ......... 206/570–572; 606/92, 86; D24/227, 229
See application file for complete search history.

(56) References Cited

U.S. PATENT DOCUMENTS

| D213,934 S | * | 4/1969 | Folkman ....................... D24/99 |
| 3,882,858 A | | 5/1975 | Klemm |
| 3,910,273 A | * | 10/1975 | Arlers ....................... 128/218 P |
| 4,011,944 A | * | 3/1977 | Cooley et al. ............... 206/557 |
| 4,128,173 A | * | 12/1978 | Lazarus et al. .............. 206/570 |

(Continued)

FOREIGN PATENT DOCUMENTS

| WO | 9704657 | 2/1997 |
| WO | 9918894 | 4/1999 |

OTHER PUBLICATIONS

Interventional Radiologic Procedures with CT Guidance in Cancer Pain Management; Afshin Gangi, MD et al.; Scientific Exhibit, vol. 16, No. 6, pp. 1289-1306.

(Continued)

*Primary Examiner*—Eduardo C. Robert
*Assistant Examiner*—Michael J Araj
(74) *Attorney, Agent, or Firm*—Brinks Hofer Gilson & Lione

(57) ABSTRACT

An apparatus and method for performing vertebroplasty are provided. In one embodiment of the invention, there is provided a kit for performing vertebroplasty having two trays, each tray having the necessary components for performing vertebroplasty via each pedicle of the damaged vertebrae. Each tray is sterilized, so that if the vertebroplasty performed via one pedicle is sufficient, then the second tray can be saved for later use. In another embodiment, each tray within the kit has two cements, each cement having different imaging properties, such that each cement will appear different when viewed with an imaging device in the lateral plane and/or will be viewable when overlapping. A presently preferred embodiment involves two trays having methylmethacrylate powder but each tray has a different amount of opacifier, either as supplied or added by the vertebroplasty professional, such that when each cement is mixed and injected, each cement is visible when exposed to X-ray lateral fluoroscopy. A method is also provided that utilizes the kit, and which allows a medical professional to monitor a second injection of cement via the second pedicle and thus reduce the risk of spinal cord compression or venous filling due to unwanted flow of cement into the spinal canal.

2 Claims, 9 Drawing Sheets

U.S. PATENT DOCUMENTS

| | | | |
|---|---|---|---|
| 4,149,635 A * | 4/1979 | Stevens | 206/370 |
| 4,341,691 A | 7/1982 | Anuta | |
| 4,404,327 A | 9/1983 | Crugnola et al. | |
| D276,462 S * | 11/1984 | Villarreal | D24/31 |
| 4,554,686 A * | 11/1985 | Baker | 623/16 |
| 4,592,356 A | 6/1986 | Gutierrez | |
| 4,720,881 A * | 1/1988 | Meyers | 5/434 |
| 4,741,330 A | 5/1988 | Hayhurst | |
| 4,774,948 A | 10/1988 | Markham | |
| 4,790,329 A | 12/1988 | Simon | |
| 4,791,150 A | 12/1988 | Braden et al. | |
| 4,799,495 A | 1/1989 | Hawkins et al. | |
| 4,837,279 A | 6/1989 | Arroya | |
| 4,843,112 A | 6/1989 | Gerhart et al. | |
| 4,931,059 A | 6/1990 | Markham | |
| 4,973,168 A | 11/1990 | Chan | |
| 5,084,043 A * | 1/1992 | Hertzmann et al. | 606/3 |
| 5,127,916 A | 7/1992 | Spencer et al. | |
| 5,147,308 A * | 9/1992 | Singer | 604/117 |
| 5,170,804 A * | 12/1992 | Glassman | 128/849 |
| 5,207,679 A | 5/1993 | Li | |
| 5,240,415 A * | 8/1993 | Haynie | 433/216 |
| 5,304,586 A | 4/1994 | Hammesfahr et al. | |
| 5,336,699 A | 8/1994 | Cooke et al. | |
| 5,367,002 A | 11/1994 | Huang et al. | |
| 5,396,897 A | 3/1995 | Jain et al. | |
| 5,422,067 A * | 6/1995 | Barney | 422/20 |
| 5,441,152 A * | 8/1995 | Estes | 206/570 |
| 5,476,880 A | 12/1995 | Cooke et al. | |
| 5,506,257 A * | 4/1996 | Macleod et al. | 514/422 |
| 5,512,610 A | 4/1996 | Lin | |
| 5,571,104 A | 11/1996 | Li | |
| 5,586,821 A | 12/1996 | Bonitati et al. | |
| 5,626,230 A * | 5/1997 | Shanley et al. | 206/571 |
| 5,645,347 A * | 7/1997 | Draenert | 366/242 |
| 5,676,146 A | 10/1997 | Scarborough | |
| 5,681,872 A | 10/1997 | Erbe | |
| 5,690,618 A * | 11/1997 | Smith et al. | 604/232 |
| 5,728,122 A | 3/1998 | Leschinsky et al. | |
| 5,749,887 A | 5/1998 | Heske et al. | |
| 5,779,053 A * | 7/1998 | Partika et al. | 206/570 |
| 5,795,922 A | 8/1998 | Demian et al. | |
| 5,800,445 A | 9/1998 | Ratcliff et al. | |
| 5,817,074 A * | 10/1998 | Racz | 604/272 |
| 5,847,046 A * | 12/1998 | Jiang et al. | 524/42 |
| 6,012,586 A * | 1/2000 | Misra | 206/571 |
| 6,020,396 A | 2/2000 | Jacobs | |
| 6,040,408 A | 3/2000 | Koole | |
| 6,080,801 A | 6/2000 | Draenert et al. | |
| 6,158,437 A * | 12/2000 | Vagley | 128/898 |
| 6,231,615 B1 | 5/2001 | Preissman | |
| 6,241,734 B1 * | 6/2001 | Scribner et al. | 606/93 |
| 6,273,916 B1 | 8/2001 | Murphy | |
| 6,450,973 B1 | 9/2002 | Murphy | |
| 6,488,667 B1 | 12/2002 | Murphy | |
| 6,585,677 B2 | 7/2003 | Cowan et al. | |
| 6,749,595 B1 | 6/2004 | Murphy | |
| 6,752,791 B2 | 6/2004 | Murphy et al. | |
| 2003/0181807 A1 | 9/2003 | Murphy et al. | |
| 2003/0204248 A1 | 10/2003 | Murphy | |
| 2004/0009459 A1 | 1/2004 | Anderson et al. | |
| 2004/0030278 A1 | 2/2004 | Cowan et al. | |
| 2004/0070253 A1 | 4/2004 | Murphy et al. | |

OTHER PUBLICATIONS

Spinal Metastases: Indications for and Results of Percutaneous Injection of Acrylic Surgical Cement; Alain Weill, M.D et al.; Radiology; vol. 199, No. 1, pp. 241-247.

Percutaneous Vertebroplasty Guided by a Combination of CT and Fluoroscopy; Afshin Gangi et al.; American Journal of Neuroradiology; vol. 15, Jan. 1994; pp. 83-86.

Percutaneous Polymethylmethacrylate Vertebroplasty in the Treatment of Osteoporotic Vertebral Body Compression Fractures: Technical Aspects; Mary E. Jensen et al.; American Journal of Neuroradiology; vol. 18, Nov. 1997; pp. 1897-1904.

Percutaneous Vertebroplasty for Osteolytic Metastases and Myeloma: Effects of the Percentage of Lesion Filling and the Leakage of Methyl Methacrylate at Clinical Follow-up; Anne Cotten, M.D. et al.; Radiology; Aug. 1996; pp. 525-530.

Percutaneous Vertebroplasty: Indications, Technique, and Complications; C. Depriester et al.; Interventional Neuroradiology, Conners & Wojak, W.B. Saunder Publ., 1999; Chapter 29, pp. 346-356.

Percutaneous Vertebroplasty with Polymethylmethacrylate; Technique, Indications, and Results; Hervé Deramond, M.D. et al.; Interventional Procedures in Musculoskeletal Radiology; vol. 36, No. 4, May 1998; pp. 533-546.

Percutaneous Vertebroplasty: State of the Art; Anne Cotten, M.D. et al; Scientific Exhibit, vol. 18, No. 2, Mar.-Apr. 1998; pp. 311-323.

Percutaneous Vertebroplasty Guided by a Combination of CT and Fluoroscopy; A. Gangi, B. Kastler, & J. Dietemann; AJNR; vol. 15, Jan. 1994; pp. 83-86.

Regulatory perspective on characterization and testing of orthopedic bone cements; H. Demian, & K. McDermott; Biomaterials; vol. 19, 1998; pp. 1607-1618.

Radioplaque Bone Cement; Howmedica Inc.; Product Information.

Zimmer Bone Cement—Dough-Type; Zimmer; Product Information.

Morganstern Prostate Stabilization Set; Medical Device Technologies, Inc.; Product Information.

Alan Hammond, Lee H. Riley III, Philippe Gailloud, David A. Nussbaum, Monica Watkins, and Kieran J. Murphy, "Treatment Considerations for Vertebroplasty in Men," *AJNR Am J Neuroradiol* 25:639-641, Apr. 2004.

Doris D. M. Lin, MD, PhD, Philippe Gailloud, MD, and Kieran J. Murphy, MD, FRCPC, "Percutaneous Vertebroplasty in Benign and Malignant Disease," *Nurosurgery Quarterly*, 11(4):290-301, 2001.

Kieran J. Murphy, MD, FRCPC, and Doris D. M. Lin, MD, PhD, "Vertebroplasty: A Simple Solution to a Difficult Problem," *Journal of Clinical Densitometry*, 4(3): 189-197, Fall 2001.

David A. Nussbaum, MS, Philippe Gailloud, MD, and Kieran Murphy, MD, "The Chemistry of Acrylic Bone Cements and Implications for Clinical Use in Image-guided Therapy," *J Vasc Interv Radiol* 15:121-26, Feb. 2004.

Cristiana Vasconcelos, Philippe Gailloud, Norman J. Beauchamp, Donald V. Heck, and Kieran J. Murphy, "Is Percutaneous Vertebroplasty without Pretreatment Venography Safe? Evaluation of 205 Consecutive Procedures," *AJNR Am J Neuroradiol*, 23:913-917, Jun./Jul. 2002.

\* cited by examiner

APPARATUS FOR STRENGTHENING VERTEBRAL BODIES

RELATED APPLICATION INFORMATION

This is a continuation-in-part application of U.S. patent application Ser. No. 09/425,480 filed Oct. 22, 1999, now U.S. Pat. No. 6,273,916.

BACKGROUND OF THE INVENTION

1. Field of the Invention

The present invention relates to vertebroplasty and a method and apparatus for strengthening vertebral bodies.

2. Description of the Prior Art

Percutaneous vertebroplasty is a technique involving the injection of a biomaterial into a vertebral body in order to treat the defects therein. It is performed using a set of surgical equipment assembled to complement such a procedure. For example, it is necessary to have equipment for prepping the patient's skin in order to provide antimicrobial effectiveness to the skin overlying the vertebrae. Equipment is also required to maintain the surgical area as clean and sterile as possible to help reduce the risk of infection. Equipment is further required to anaesthetize the patient to produce a reversible loss of sensation in the surgical area of the body, in preparation for incision. The incision is made by any suitable surgical equipment capable of cutting anatomical tissue. Also, it is necessary to have equipment with a sharp end able to penetrate the vertebral body for injection of the biomaterial into the vertebral body. Further, it is necessary to provide equipment for preparation of the biomaterial and delivery into the vertebral body.

Before a procedure can be performed, it is necessary to assemble all of the equipment that is likely to be needed for the procedure. Typically, the extent and complexity of the treatment is unknown prior to the procedure, that is, whether injections of biomaterial will occur into one, or both pedicles. Given this uncertainty, more equipment than necessary can be assembled to allow for a second injection. However, should the nature of the vertebral defect only require injections from one side of the vertebrae, then the unused biomaterial and equipment is wasted. Furthermore, after the equipment has been provided and arranged for use, it must be kept clean and sterile. Proper equipment sterilization is elementary before any procedure, to ensure complete elimination of microbial viability thus reducing risk of infection. If the equipment is laid out too far in advance of a procedure, the chances of maintaining sterility decreases. Contaminated or unused equipment is either replaced or discarded, thus making for a very time consuming and costly exercise. It is therefore desirable to assemble only the necessary equipment as close to the time of the procedure as possible.

There exists equipment for preparation and delivery of biomaterial into the vertebral body. For example, one of the more popular systems is a bone cement delivery system, available from Parallax-Medical, California, U.S.A. This reference is available at http://www.parallax-medical.com/products.html. This system contemplates that two injections will be needed in each procedure, thus the cement delivery system is pre-packaged to include pairs of equipment. However, this system is designed for any bone filling procedure and thus does not include all of the necessary components for percutaneous vertebroplasty.

Also disclosed is a commercially available set of equipment specifically designed for surgical procedures of the spine. It is contemplated that the equipment present in the kit not essential to the percutaneous vertebroplasty procedure will be unused. In sum, the present commercially available kits are not directed towards percutaneous vertebroplasty procedures, thus resulting in equipment being wasted. It would therefore be desirable to provide a set of sterilized equipment, packaged as a single unit, and containing all of the equipment necessary for performing only one injection in a percutaneous vertebroplasty procedure.

SUMMARY OF THE INVENTION

It is therefore an object of the present invention to provide a novel method and apparatus for strengthening vertebral bodies which obviates or mitigates at least one of the disadvantages of the prior art.

In one aspect of the invention there is provided a kit for use in performing vertebroplasty comprising a first bone cement for strengthening a vertebral body, the first bone cement having a first imaging property and a second bone cement for strengthening the vertebral body having a second imaging property. When the vertebral body is exposed to an imaging device, an injection of the second bone cement is distinguishable from an injection of the first bone cement.

An apparatus and method for performing vertebroplasty are provided. In one embodiment of the invention, there is provided a kit for performing vertebroplasty having two packs, each pack having the necessary components for performing vertebroplasty via each pedicle of the damaged vertebrae. Each pack is sterilized, so that if the vertebroplasty performed via one pedicle is sufficient, then the second pack can be saved for later use. In another embodiment, each pack within the kit has two cements, each cement having different imaging properties, such that each cement will appear different when viewed with an imaging device in the lateral plane and/or will be viewable when overlapping. A presently preferred embodiment involves two packs having methylmethacrylate powder but each pack has a different amount of opacifier to be added to the powder, such that when each cement is mixed and injected, each cement is visible when exposed to X-ray lateral fluoroscopy. A method is also provided that utilizes the kit, and which allows a medical professional to monitor a second injection of cement via the second pedicle and thus reduce the risk of spinal cord compression due to unwanted flow of cement into the spinal cord, or nerve compression.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

Figure 1:
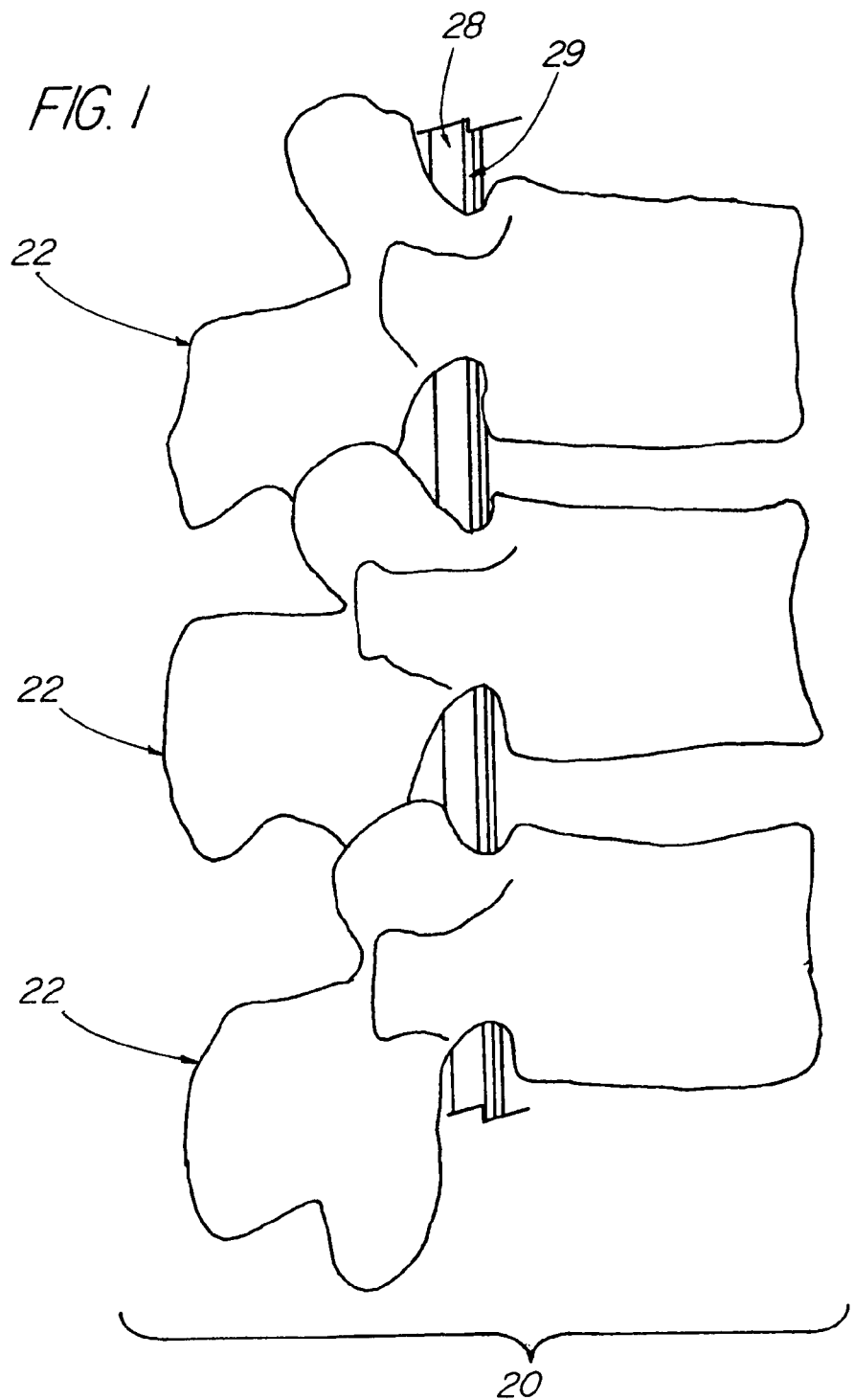
FIG. 1 illustrates a lateral view of three normal vertebrae.
Figure 2:
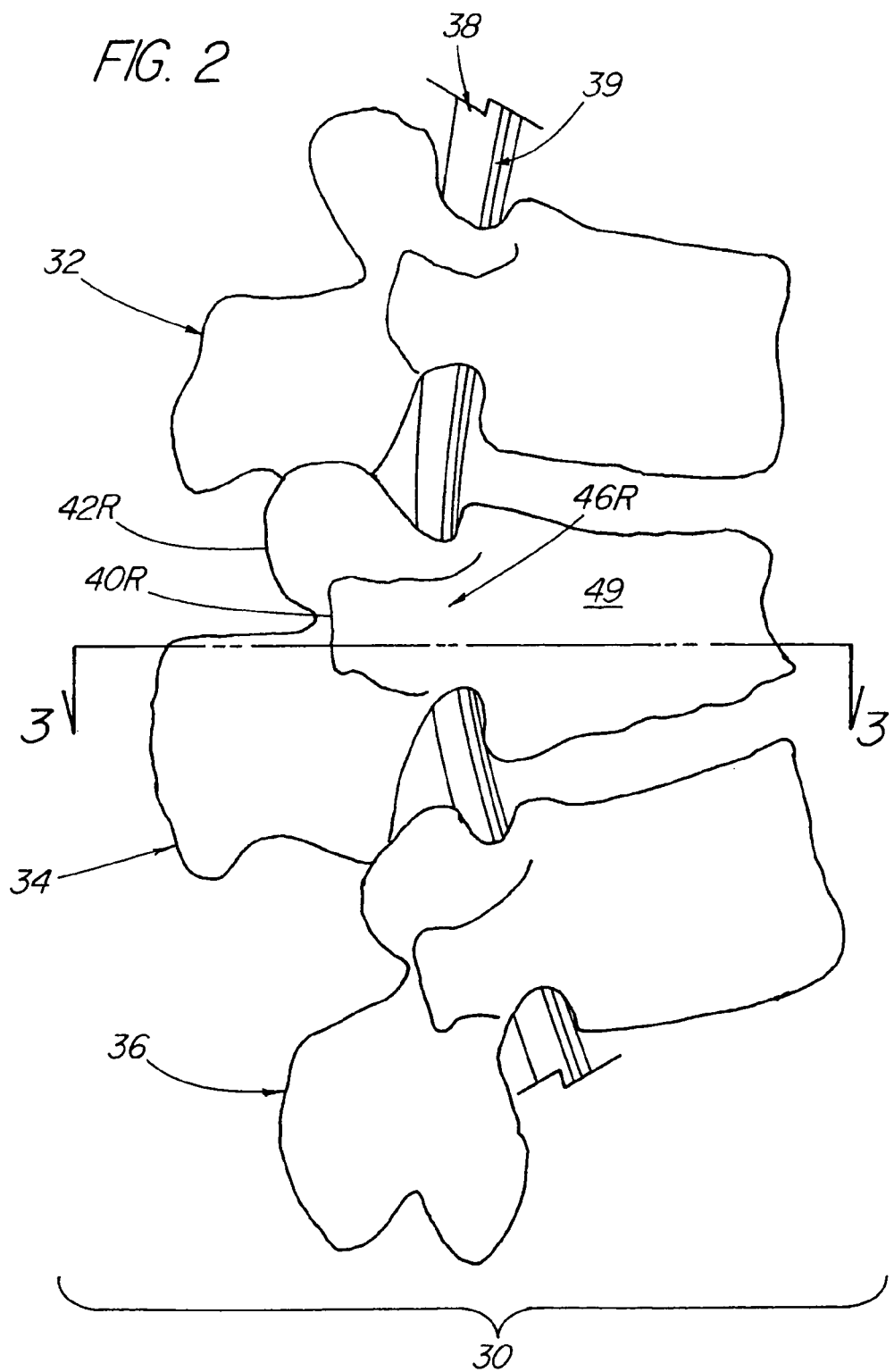
FIG. 2 illustrates a lateral view of three vertebrae wherein the middle vertebral body has a condition suitable for treatment by vertebroplasty.

Before discussing embodiments of the present invention, various components of vertebrae and the spine will be discussed. FIG. 1 is a right lateral view of a segment 20 of a normal spine. Segment 20 includes three vertebrae 22. The spinal cord 28 and epidural veins 29 run through the spinal canal of each vertebrae 22. In contrast to segment 20 of FIG. 1, FIG. 2 shows a right lateral view of a segment 30 of a spine wherein at least one of the vertebra has a condition suitable for treatment by vertebroplasty. Segment 30 includes a first vertebra 32, a compressed middle vertebra 34 and a third vertebra 36. Spinal cord 38 and epidural veins 39 run through the spinal canal of each vertebrae 32, 34 and 36.

Figure 3:
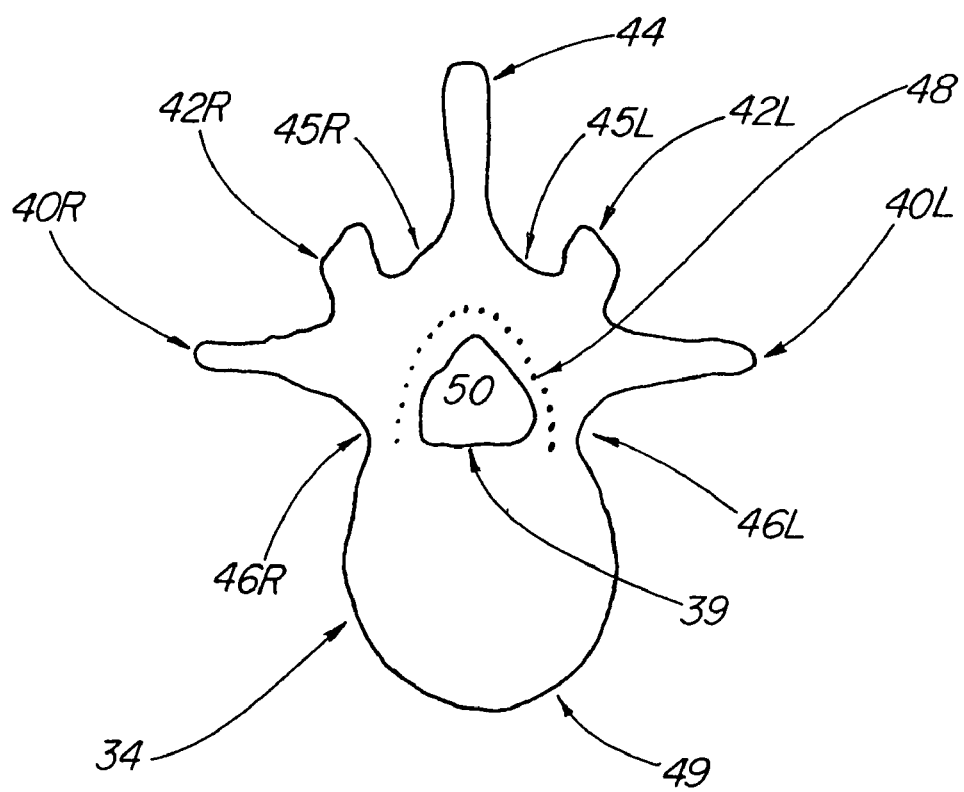
FIG. 3 illustrates an axial view of the compressed vertebral body through line III-III of FIG. 2.

As shown in FIGS. 2 and 3, vertebra 34 has a right and left transverse process 40R, 40L, a right and left superior articular process 42R, 42L, and a spinous process 44 at the posterior of vertebra 34. Right and left lamina 45R, 45L lie intermediate spinous process 44 and superior articular processes 42R, 42L, respectively. Right and left pedicles 46R, 46L and lamina 45R, 45L cooperate to form the vertebral arch 48. The vertebral body 49 is located at the anterior of vertebra 34, and is joined to arch 48 at pedicles 46R, 46L. Arch 48 and vertebral body 49 define the spinal canal 50 through which spinal cord 38 passes. Epidural veins 39 lie between spinal cord 38 and vertebral body 48. As seen in FIG. 2, vertebral body 49 is compressed as a result of any condition suitable for treatment by vertebroplasty. Such conditions generally include benign osteoporotic fractures, malignant metastatic disease and benign tumours of the bone.

Figure 4:
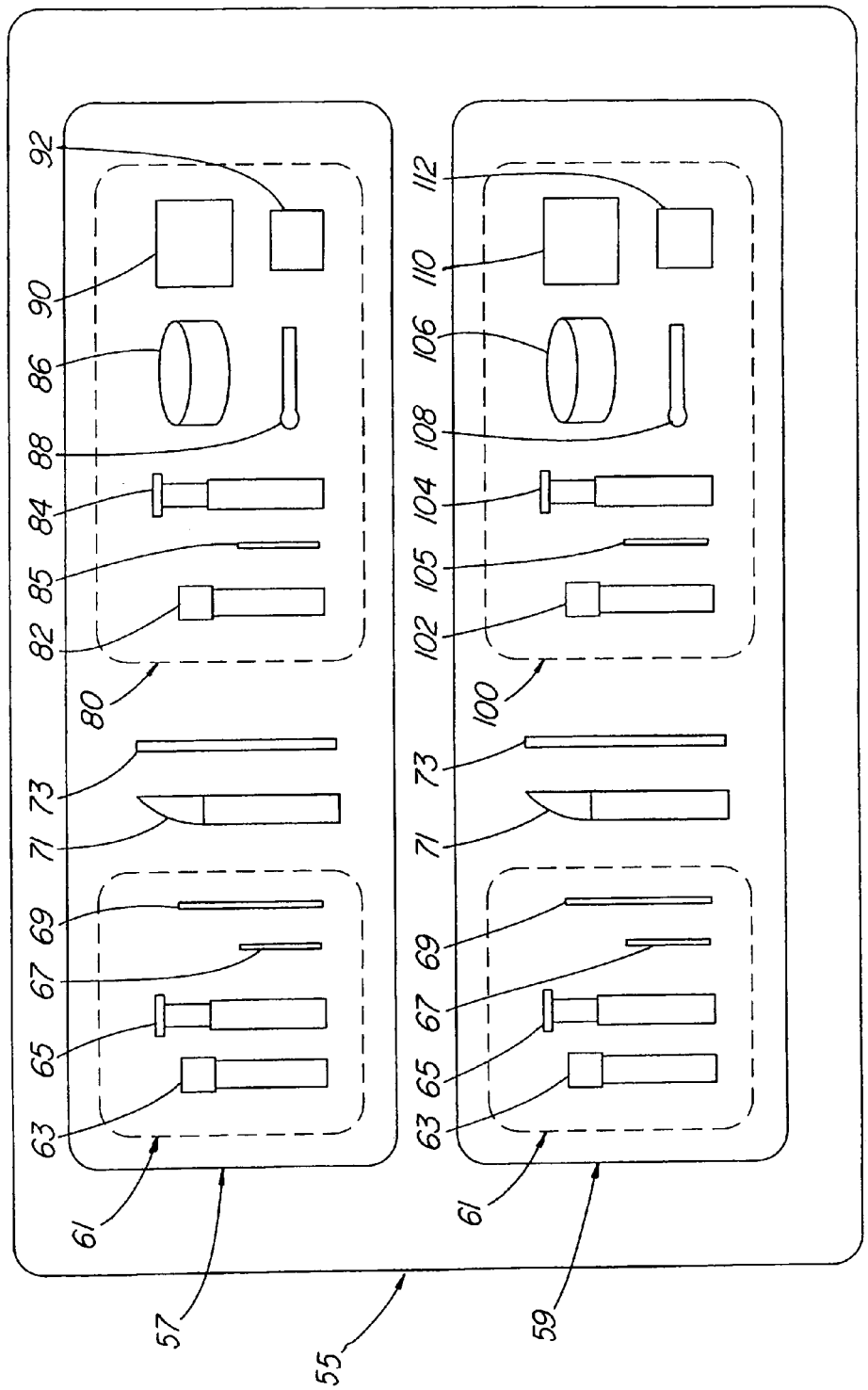
FIG. 4 illustrates a schematic representation of a kit for vertebroplasty in accordance with an embodiment of the invention.

Referring now to FIG. 4, a kit, in accordance with an embodiment of the invention, for the strengthening of vertebral body 44 is indicated generally at 55. As will be understood by those of skill in the art, the individual items in FIG. 4 are known, and are drawn in a simplified form and kit 55 should not be construed as limited to the representation of FIG. 4. Kit 55 includes a first tray 57 and a second tray 59. Kit 55 and each tray 57, 59 therein are housed within a sterile packaging suitable for refrigeration and/or storage until use. Each tray 57, 59 has a local anaesthesia assembly 61, including a vial of local anaesthesia 63, a syringe 65 for administering the anaesthesia, a needle 67 for anaesthesia aspiration and a long needle 69 for anaesthesia injection. It is presently preferred that vial 63 has ten cubic-centimeters of 1% lidocaine without adrenaline, and accordingly that syringe 65 is a ten cc syringe. It is also presently preferred that needle 67 is sixteen gauge, while long needle 69 is twenty-two gauge. It will be understood that anaesthesia assembly 61 consists of well-known components, and that other components can be substituted, as desired.

Each tray 57, 59 also includes a scalpel 71 suitable for making an incision to perform vertebroplasty. It is presently preferred that scalpel 71 is disposable and has a number-eleven blade. It will be understood that any scalpel or other functionally equivalent surgical tool suitable for vertebroplasty can be used, as will occur to those of skill in the art.

Trays 57, 59 also include at least one vertebroplasty needle 73. Where kit 55 is for use on a lumbar vertebral body, then it is generally preferred that an eleven gauge vertebroplasty needle 73 is included. Where kit 55 is for use on a thoracic vertebral body, then it is generally preferred that a thirteen gauge vertebroplasty needle 73 is included. It will be understood, however, that various sizes and combinations of vertebroplasty needles 73 can be included into each tray 57, 59 to offer greater flexibility for each kit 55, as desired and/or required for a particular vertebroplasty operation. One suitable vertebroplasty needle is the Cook needle, model DBBN-10(11)(13)-10.0(15.0)-m1(m2) from Cook Inc., Bloomington Ind.

Tray 57 also includes the ingredients for a first bone cement for strengthening a vertebral body and which has a first imaging property. In a present embodiment, the ingredients and mixing devices for the first bone cement are provided in a first cement assembly 80. First cement assembly 80 includes monomer liquid 82 in a vial, a monomer compatible aspiration syringe 84, a monomer aspiration needle 85, a mixing bowl 86, a mixing spatula 88, a polymer powder 90, and a first opacifier 92.

It is believed that the vial of monomer liquid 82 should contain from about five cubic-centimeters to about twenty cubic-centimeters of monomer. Any monomer that is intended for use with a corresponding polymer powder 90 can be used. For example, in Osteobond there is a liquid component of 99.25% methylmethacrylate monomer, 0.75% N, N-dimethyl-p-toluidine and 75±10 ppm hydroquinone in Osteobond Copolymer Bone Cement from Zimmer Inc., 1800 West Center Street, Warsaw Ind. 46580. Other suitable monomer liquids are included in other bone cements as offered by the various bone cement suppliers. Preferably, the vial contains from about seven cubic-centimeters to about fifteen cubic-centimeters of monomer liquid 82. More preferably, the vial contains from about ten cubic-centimeters to about thirteen cubic-centimeters of monomer liquid 82. It is presently preferred, however, that the vial contains from about twelve cubic-centimeters of monomer liquid 82. Overall, it will be understood that any composition and/or quantity of monomer liquid 82 can be provided that allows a radiologist or other vertebroplasty professional to prepare polymer powder 90 with a desired consistency.

Monomer aspiration syringe 84 is accordingly sized to accommodate the volume of monomer liquid 82. Preferably, syringe 84 is DMSO (dimethylsulphoxide) compatible, which is designed so that the plunger does not swell when it contacts monomer liquid 82. A suitable source for syringe 84 is MTI, Micro Therapeutics Inc., 2 Goodyear, Irvine Calif. 92618.

A suitable mixing bowl 86 is a small disposable plastic bowl, such the "gent-l-kare" sterile one quart single-use disposable utility bowl made by Premium Plastics Inc., Chicago Ill. 60616. Both mixing bowl 86 and mixing spatula 88 are made from a material that is suitable for use in the mixing of the bone cement, as is known to those of skill in the art. Other suitable mixing devices, such as the closed mixing system known as the "vacuum cement mixing" device supplied by Howmedica can be used, as will occur to those of skill in the art.

Polymer powder 90 is packaged in any suitable sterile sachet. However, any bag or storage means can be used and which are suitable for holding from about five grams to about forty grams of methylmethacrylate. Preferably, polymer powder 90 is from about ten grams to about thirty grams of methylmethacrylate. More preferably, polymer powder 90 is from about twelve grams to about twenty grams of methylmethacrylate. It is presently preferred, however, that polymer powder 90 is about eighteen grams of methylmethacrylate.

It will now be apparent that the foregoing monomer liquid 82 and polymer powder 90 is obtainable in Osteobond. Other suitable bone cements include calcium carbonate, calcium phosphate, zirconium, or oxalate or hydroxyappatite derivatives, as will be understood by those of skill in the art.

First opacifier 92 is packaged in a sterile sachet or equivalent storage means, In the present embodiment, where polymer powder 90 is methylmethacrylate then first opacifier 92 is barium powder. It is believed that there should be a mass of barium of from about ten percent to about fifty percent of the mass of the methylmethacrylate. Preferably, there should be a mass of barium of from about fifteen percent to about forty-five percent of the mass of methylmethacrylate. More preferably, there should be a mass of barium powder of from about twenty percent to about forty percent of the mass of methylmethacrylate. It is presently preferred, however, that there should be a mass of barium of about one-third of the mass of methylmethacrylate, and thus, where there are eighteen grams of methylmethacrylate there should be about six grams of barium. In general, it will be understood that a sufficient amount of barium should be added to the first cement such that a suitable radio-opacity is provided without degrading the physical properties of the first cement. Other suitable opacifiers, such as calcium phosphate, calcium carbonate, tantalum, tungsten or zirconium can be used, as will occur to those of skill in the art.

Tray 59 includes the ingredients for a second bone cement for strengthening a vertebral body that is compatible and/or usable with the first bone cement and which has a second imaging property. In a present embodiment, the ingredients and mixing devices for the second bone cement are provided in a second cement assembly 100. Second cement assembly 100 includes monomer liquid 102 in a vial, a monomer aspiration syringe 104, a monomer aspiration needle 105 a mixing bowl 106, a mixing spatula 108, polymer powder 110, and a second opacifier 112.

It is presently preferred that monomer liquid 102, syringe 104, needle 105, bowl 106, spatula 108 and powder 110 are the same as liquid 82, syringe 84, bowl 86, spatula 88 and powder 90, respectively, from tray 57.

However, second opacifier 112 has a different composition and/or quantity from first opacifier 92, so that when it is mixed into a second bone cement the second bone cement has a different imaging property from the first bone cement. Second opacifier 112 is packaged in a bag, similar to first opacifier 92. In the present embodiment, second opacifier 112 is also barium but has a different, preferably higher, quantity than first opacifier 92. It is believed that there should be about fifteen percent to about three-hundred percent more barium in second opacifier 112 than first opacifier 92. Preferably, there should be about there should be about thirty percent to about two-hundred-and-fifty percent more barium in second opacifier 112 than first opacifier 92. More preferably, there should be about forty percent to about two-hundred percent more barium in second opacifier 112 than first opacifier 92. It is presently preferred, however, that there should be about one-hundred-and-eighty percent more barium powder in second opacifier 112 than first opacifier 92. Thus, in a presently preferred embodiment, there is about eleven grams of barium powder in second opacifier 112 to contrast the six grams of barium powder in first opacifier 92. In general, it will be understood that a sufficient amount of barium should be added to polymer powder 110 to provide a radio-opacity that differs from the radio-opacity of the first cement, but without degrading the physical properties of the second cement.

Figure 5:
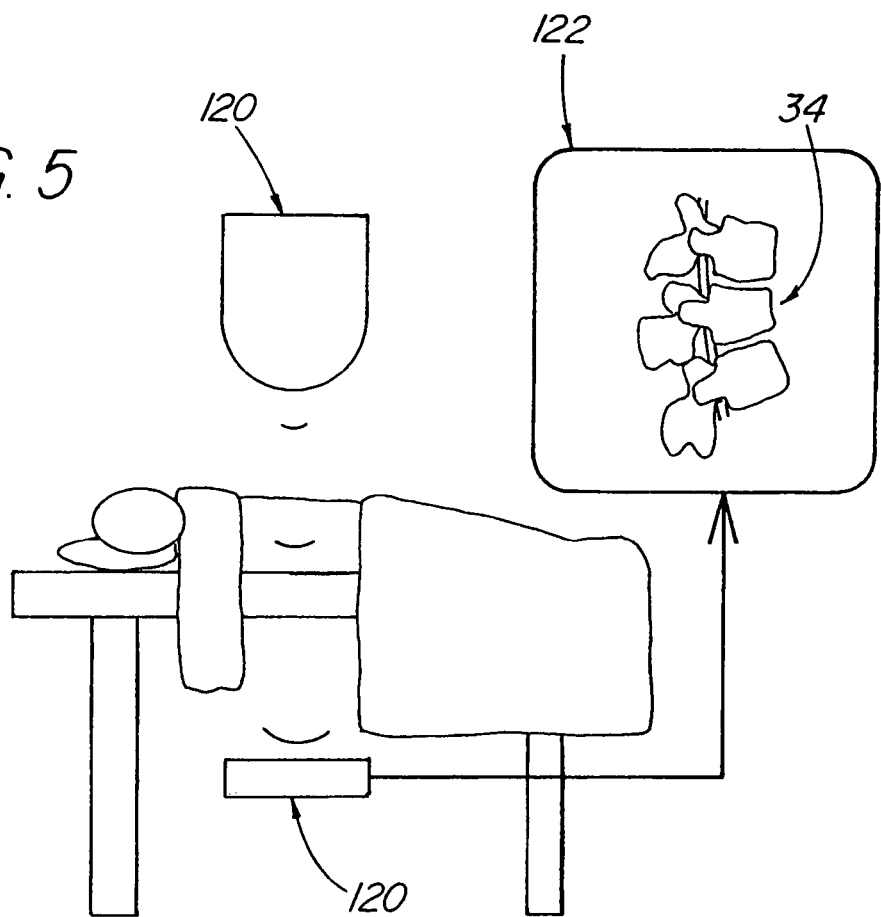
FIG. 5 illustrates a schematic representation of an operating table and an imaging device for performing vertebroplasty, showing a patient lying prone and prepped for vertebroplasty and an imaging display showing the lateral view of FIG. 2.
Figure 6:
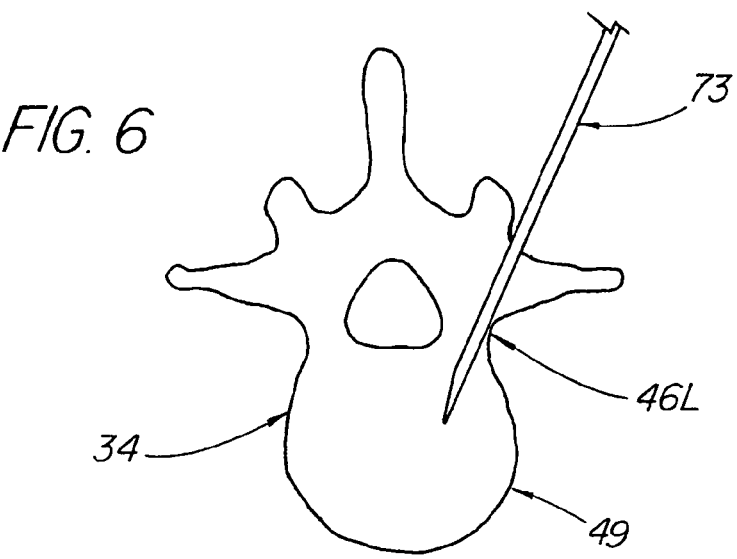
FIG. 6 illustrates the axial view of FIG. 3 showing the insertion of a vertebroplasty needle through the left pedicle.
Figure 7:
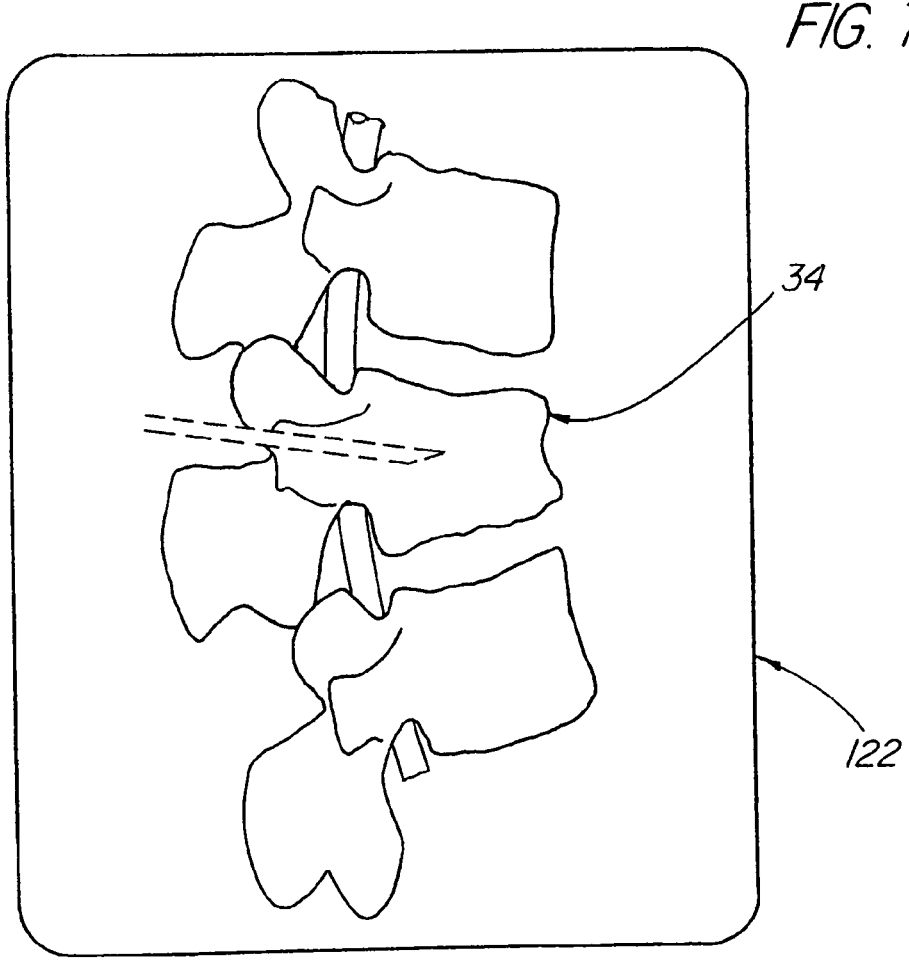
FIG. 7 illustrates the lateral view of FIG. 6, as projected by the imaging device.

A method for performing vertebroplasty in accordance with an embodiment of the invention will now be discussed, utilizing kit 55 and performed on a patient having vertebrae 34. Referring now to FIG. 5, the patient is placed in the prone position so that vertebrae 34 is within the field of an imaging device 120, which in a present embodiment is an X-Ray projection fluoroscopy imaging device. Other imaging devices can be used, as will occur to those of skill in the art. When imaging device 120 is 'on', vertebrae 34 is projected onto display 122. For purposes of explaining the present embodiment, vertebrae 34 is projected onto display 122 from the same lateral view as shown in FIG. 2. The skin overlying vertebrae 34 is prepped and draped in the usual manner with sterile technique. Next, the seal on kit 55 is broken, and the seal on tray 57 is broken. Anaesthesia assembly 61 is opened and utilized so that anaesthesia 63 is injected into the skin underlying fat and into the periosteum of the pedicle to be entered. For purposes of explaining the present method, it will be assumed that left pedicle 46L will be entered first. Next, using scalpel 71, a skin incision of about five millimeters is made with scalpel 73. As shown in FIGS. 6 and 7, at this point vertebroplasty needle 73 is inserted into the incision and passed down left pedicle 46L, preferably until it enters the vertebral body and reaches the junction of the anterior and middle thirds.

Figure 8:
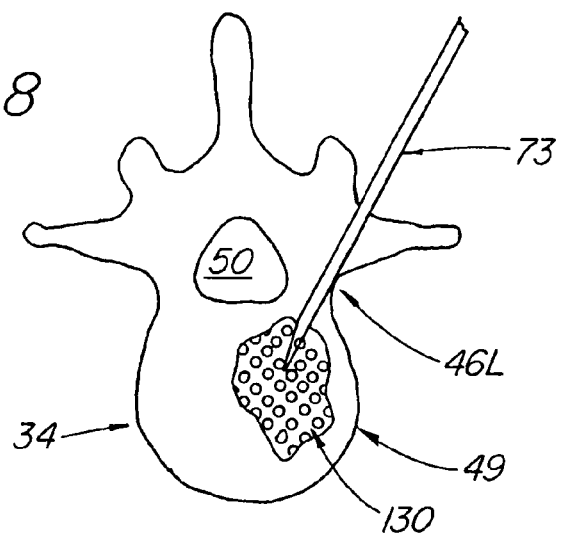
FIG. 8 illustrates the axial view of FIG. 6 showing the injection of a first cement having a first imaging property into the vertebral body.
Figure 9:
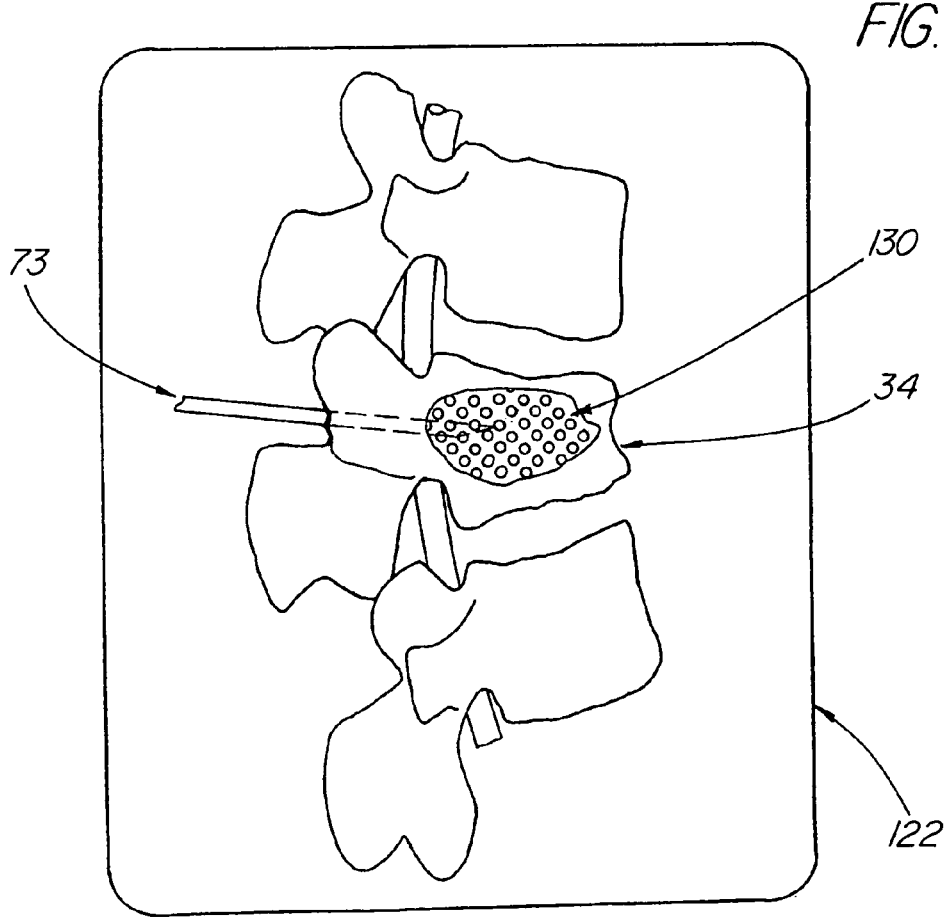
FIG. 9 illustrates the lateral view of FIG. 8, as projected by the imaging device.

At this point, first cement assembly 80 is opened. Powder 90 and first opacifier 92 are placed in mixing bowl 86 and monomer 82 is injected into mixing bowl 86 using syringe 84. A first cement for strengthening a vertebral body and having a first imaging property is thus prepared by mixing the contents of mixing bowl 86 with spatula 88. In the present embodiment, the first imaging property is determined by the quantity of first opacifier 92 within the first cement. As shown in FIGS. 8 and 9, the first cement is injected into vertebral body 49 via left pedicle 46L through needle 73, the first cement being indicated at 130. Opacifier 92 allows first cement 130 to be detected by imaging device 120 and is thus viewable on display 122 as having a first imaging property. The first imaging property is represented in first cement 130 as a pattern of small circles. Accordingly, the quantity and flow-route of first cement 130 is monitored on display 122, as shown in FIG. 9.

At this point, a decision can be made as to whether a sufficient quantity of first cement 130 that has been injected. This decision is made using known criteria and is typically made by the radiologist, physician or other vertebroplasty professional who is performing the method. If it is determined that enough cement has been injected to provide the desired strength to vertebral body 34, then the treatment method is complete and the patient is prepared for removal from the X-ray room and transferred to the observation area. Tray 59 is still sterile and can be placed back into refrigeration or storage for use on another patient at a later date.

Figure 10:
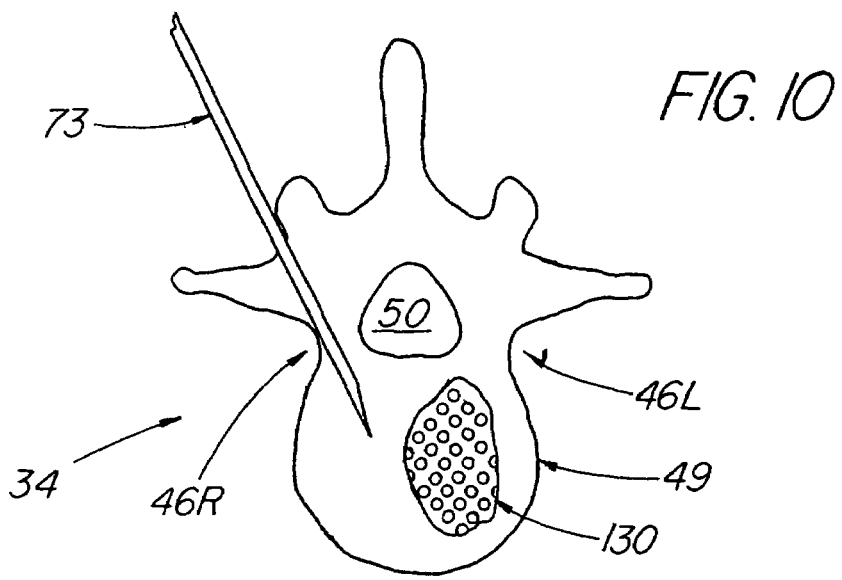
FIG. 10 illustrates the axial view of FIG. 8 showing the insertion of a vertebroplasty needle through the right pedicle.
Figure 11:
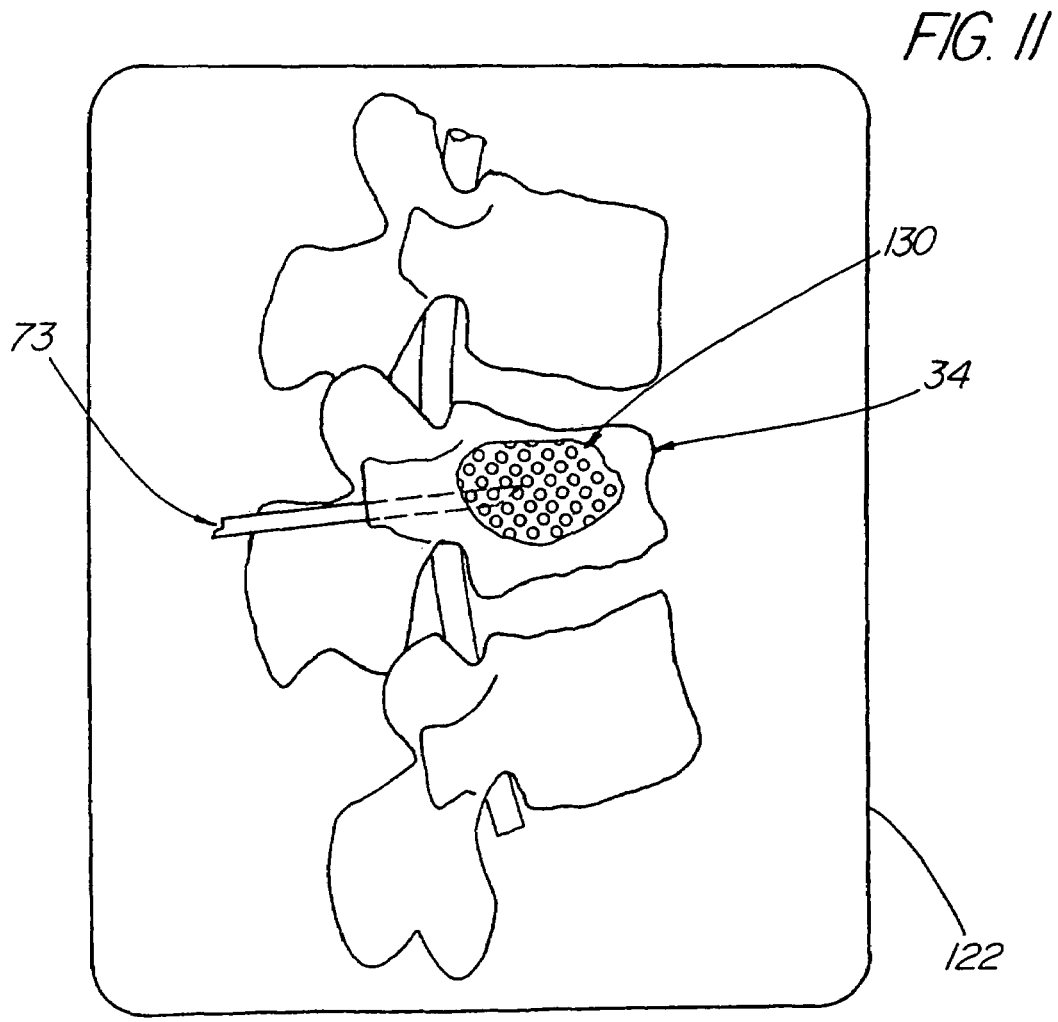
FIG. 11 illustrates the lateral view of FIG. 10, as projected by the imaging device.

If, however, it is determined that another injection is required along right pedicle 46R, then tray 59 is opened and anaesthesia assembly 61 therein is opened and anaesthesia 63 is injected into the skin posterior to right pedicle 46R. Scalpel 71 of tray 59 is then used to make the appropriate incision, and vertebroplasty needle 73 of tray 59 is inserted into vertebral body 49 via right pedicle 46R, as shown in FIGS. 10 and 11.

Figure 12:
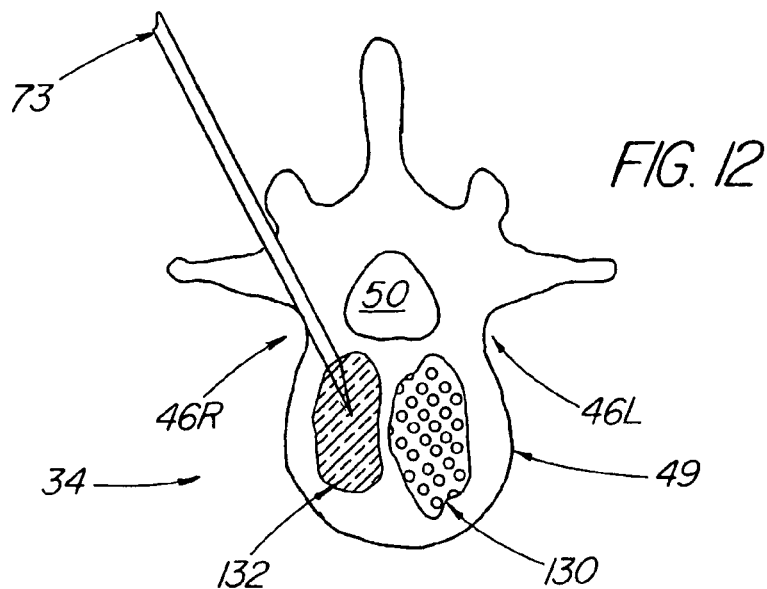
FIG. 12 illustrates the axial view of FIG. 10 showing the injection of a second cement having a second imaging property into the vertebral body; and, FIG. 13 illustrates the lateral view of FIG. 12, as projected by the imaging device.
Figure 13:
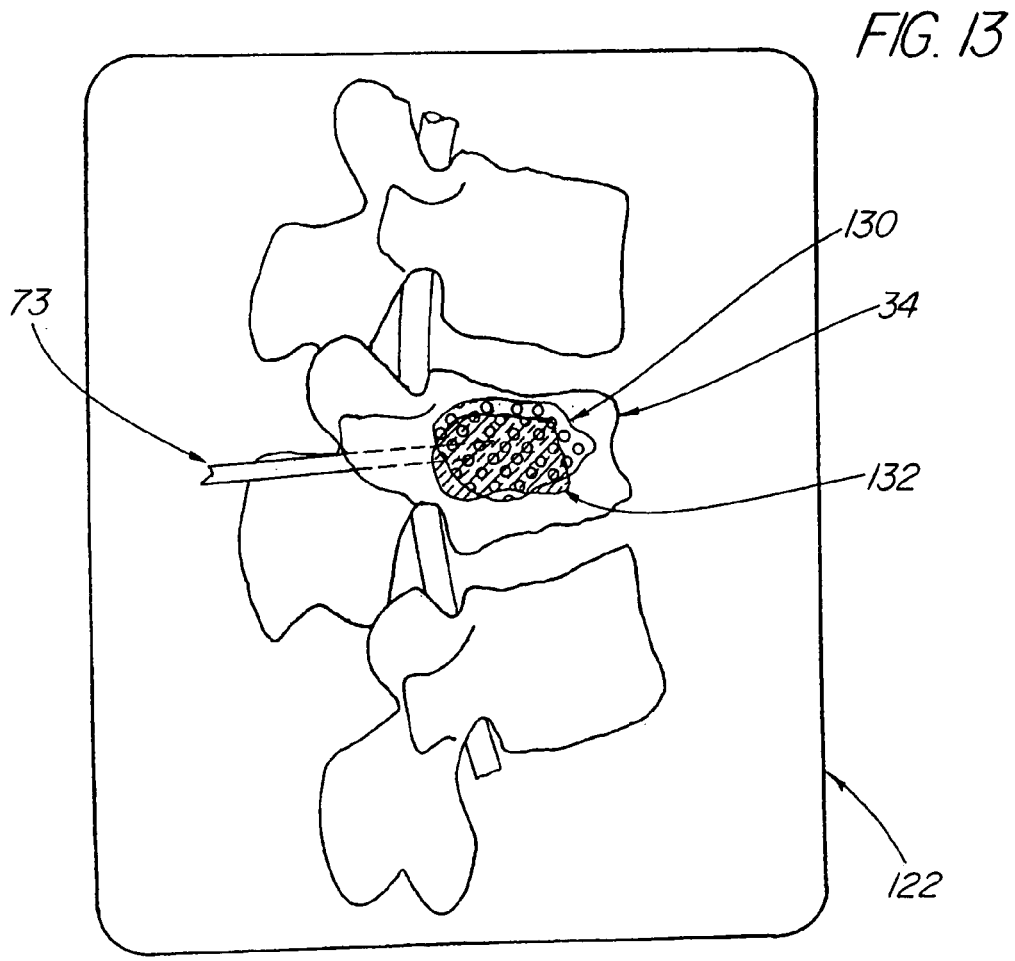

At this point, second cement assembly 100 is opened. Powder 110 and second opacifier 112 are placed in mixing bowl 106 and monomer 102 is aspirated into mixing bowl 106 using syringe 104. A second cement for strengthening a vertebral body that has a second imaging property, (which in the present embodiment has different radio-opacity), is thus prepared by mixing the contents of mixing bowl 106 with spatula 108. In the present embodiment, the second imaging property is determined by the quantity of second opacifier 112 within the second cement. As shown in FIGS. 12 and 13, the second cement is injected into vertebral body 49 via right pedicle 46R through needle 73, the second cement being indicated at 132. Opacifier 112 allows second cement 132 to be detected by imaging device 120 and is thus viewable on display 122 as having a second imaging property. The second imaging property is represented in second cement 132 as a pattern of diagonal lines. Accordingly, the quantity and flow-route of second cement 132 is monitored on display 122, as shown in FIG. 13. In particular, the quantity and flow-route of second cement 132 can be monitored in contrast to the first cement 130, due to the contrasting or different imaging properties of first cement 130 and second cement 132. By monitoring the flow-route of second cement 132, the injection of second cement 132 can be terminated before it reaches spinal canal 50 and thus reduce the likelihood of spinal cord compression and/or related damage. Once a sufficient amount of second cement 132 has been injected, the method is complete and the patient is prepared for discharge.

It should be understood that the opacifier in at least one of the first and second cements can be in the form of particles dispersed throughout the respective cement. In certain circumstances, the motion of such particles can increase the ability to detect cement motion and filling. For example, when using methylmethacrylate powder with barium, the barium can be in the form of powder and/or particles. It is presently preferred that the barium particles are about one millimeter in size, however, other particle sizes will occur to those of skill in the art. When used with an X-ray imaging system, other particles can include, for example, calcium phosphate, oxalate, zirconium, tantalum and/or tungsten. Other types of particles will occur to those of skill in the art.

It can be desired to use a first cement with a first density of radio-opaque particles, and a second cement having a second density of radio-opaque particles. Generally, it is preferred that the second cement injection has a greater density of particles than the first cement injection. Furthermore, previously discussed, it is generally preferred that the method is performed so that second cement injection appears in front of the first cement injection, as displayed on the imaging display.

It can be desired that only one of the cements has radio-opaque particles, while the other cement has a radio-opaque powder. While not necessary, it is generally preferred that the cement with the particles is used for the second injection of cement.

Other variations of how to provide two different opacifiers that will make each respective injection of each cement appear contrasting and/or different under an imaging system will occur to those of skill in the art, and are within the scope of the invention.

While the embodiments discussed herein are directed to particular implementations of the present invention, it will be apparent that the sub-sets and variations to these embodiments are within the scope of the invention. For example, kit 55 can include drapes, disinfectant and/or sponge tipped disinfectant applicators for use in the preparation of the patient prior to performing the operation. Other items of assistance during a vertebroplasty can be added to kit 55, as desired.

It is to be understood that the individual trays 57, 59 of kit 55 need not include anaesthesia assemblies, vertebroplasty needles, scalpels etc. and that it is contemplated that each tray 57, 59 need only include a first cement for strengthening a vertebral body that has a first imaging property, and a second bone cement for strengthening a vertebral body that has a second imaging property, whereupon injection thereof each cement is visible by an imaging system, such as a X-ray or other radiographic imaging system. The other items in trays 57, 59 can be obtained and/or assembled from other sources prior to performing the method.

The ability to detect motion of cement during injection can be increased where radiopaque vertebroplasty needles are used, thus allowing the detection of motion of cement as the cement travels along the length of the needle.

It will be understood that each tray 57, 59 can be packaged and/or sold separately, and/or need not be included in an entire kit 55. Furthermore, kit 55 can be sold as having two of tray 59, two of tray 57, or, as previously discussed, one tray 57 and one tray 59. By offering different combinations of kit 57 and trays 57, 59 vertebroplasty professionals can be offered kits having cements with imaging properties that are personally preferred by the professional, and/or allow the purchase of additional individual trays that complement left-over individual trays from procedures that only required the use of one tray.

It is contemplated that the first and second bone cements can also be bone cements that are bioactive, integratable, stimulate bone growth and/or are resorbable. Orthocomp™ cement by Orthovita of 45 Great Valley Parkway, Malvern Pa. 19355 is one such cement. Other suppliers of such cements include Howmedica/Stryker of 6300 Sprinkle Road, Kalamazoo, Mich. 49001, and Codman/Depuy of 325 Paramount Drive Raynham Mass. 02767. It is contemplated that as other suitable cements are developed and/or approved, the contents of the kit can vary to suit the surgical procedure used to inject the first and second cements.

It is also contemplated that the mechanism for injecting the cement can be automatically controlled via a computer or other controller that receives the image from the imaging device and has an output connected to the vertebroplasty needle injection mechanism. Such a controller can be programmed to determine, based on the received image, when to commence, stop or otherwise control the flow of the injection of each cement.

While the present invention teaches first and second cements having differing densities and/or distributions of particles of barium to provide different imaging properties when exposed to lateral X-ray fluoroscopy, other opacifiers and/or imaging technologies can be used, as will occur to those of skill in the art. Other imaging technologies can include, for example, magnetic resonance imaging, and computed tomography.

It will be further understood that trays 57 and 59 within kit 55 can each have completely identical components, and, optionally kit 55 can further include a separate package of opacifier to be mixed with one of the cement assemblies to provide two different cements that will have different imaging properties. Alternatively, the extra opacifier need not be provided with kit 55, but can be obtained separately by a user of kit 55. The other permutations and combinations of kit 55 will now be apparent, and are within the scope of the invention.

It will also be understood that polymer powder 90 and first opacifier 92 can be premixed and packaged in a single sachet within first tray 57. Similarly, polymer powder 110 and second opacifier 112 can also be premixed.

While the present invention is generally suitable for known conditions that are treatable with vertebroplasty, it is contemplated that the present invention can be suitable for other conditions that require similar treatment. For example, prophylactic vertebroplasty can be performed in patients with critically low bone density.

The present invention provides a novel method and kit for increasing strength of vertebral bodies. In one embodiment, there is provided a first cement for strengthening a vertebral body which has a first imaging property, and a second bone cement for strengthening a vertebral body that is compatible with the first bone cement and which has a second imaging property, such that each cement is visible during injection under the guidance of an imaging system, such as lateral X-ray fluoroscopy. By providing these two cements, vertebroplasty can be performed by injection into both pedicles of the vertebra and allow a radiologist, physician or other vertebroplasty professional to observe the flow of the cements and thus more safely and/or effectively inject cement in the vertebral body and reduce the likelihood of spinal cord compression and/or related damage. The present invention also provides a kit for performing vertebroplasty, having a first tray for performing vertebroplasty through one pedicle, and a second tray for performing vertebroplasty through a second pedicle. Each tray can have a variety of different combinations, as desired. Each tray can be used independently. Unused packages can be stored for later use and a second conventional vertebroplasty procedure can be carried out using of the second tray.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A vertebroplasty kit for use in performing vertebroplasty, said vertebroplasty kit comprising:
   a first tray of vertebroplasty injection components for performing a first vertebroplasty injection through a first pedicle of a vertebral body;
   a second tray of vertebroplasty injection components for performing a second vertebroplasty injection through a second pedicle of said vertebral body, such that said second tray of vertebroplasty injection components can remain sterile for use in another vertebral body if said first vertebroplasty injection sufficiently strengthens said vertebral body, wherein the vertebroplasty injection components comprise:
   a local anaesthesia;
   a local anaesthesia aspiration syringe;
   a local anaesthesia aspiration needle;
   a local anaesthesia injection needle;
   a liquid monomer;
   a monomer aspiration needle;
   a monomer aspiration syringe;
   a mixing bowl;
   a mixing spatula;
   a polymer powder;
   an opacifier;
   a scalpel; and
   a vertebroplasty needle.

2. A vertebroplasty kit for use in performing vertebroplasty, said vertebroplasty kit comprising:
   a first tray of vertebroplasty injection components for performing a first vertebroplasty injection through a first pedicle of a vertebral body;
   a second tray of vertebroplasty injection components for performing a second vertebroplasty injection through a second pedicle of said vertebral body, such that said second tray of vertebroplasty injection components can remain sterile for use in another vertebral body if said first vertebroplasty injection sufficiently strengthens said vertebral body, wherein the vertebroplasty injection components comprise:
   a local anaesthesia;
   a local anaesthesia aspiration syringe;
   a local anaesthesia aspiration needle;
   a local anaesthesia injection needle;
   a monomer aspiration needle;
   a monomer aspiration syringe;
   a mixing bowl;
   a mixing spatula;
   a scalpel; and
   a vertebroplasty needle.

* * * * *